(12) United States Patent
Forssmann et al.

(10) Patent No.: US 6,849,593 B1
(45) Date of Patent: Feb. 1, 2005

(54) BIFIDOGENIC PEPTIDES (75) Inventors: Wolf-Georg Forssmann, Hannover (DE); Hans-Dieter Zucht, Hannover (DE); Cornelia Liepke, Hannover (DE)

(73) Assignee: Pharis Biotec GmbH, Hanover (DE)

( * ) Notice: Subject to any disclaimer, the term of this patent is extended or adjusted under 35 U.S.C. 154(b) by 0 days.

(21) Appl. No.: 09/508,095

(22) PCT Filed: Sep. 16, 1998

(86) PCT No.: PCT/EP98/05899

§ 371 (c)(1),
(2), (4) Date: Mar. 16, 2000

(87) PCT Pub. No.: WO99/14231

PCT Pub. Date: Mar. 25, 1999

(30) Foreign Application Priority Data

Sep. 16, 1997 (DE) .......................... 197 40 604
Feb. 11, 1998 (DE) .......................... 198 05 385

(51) Int. Cl.[7] .......................... A61K 38/00; C07K 14/00
(52) U.S. Cl. .............. 514/2; 514/12; 514/14; 514/18; 435/252.8; 435/254.1; 435/255.1; 530/324; 530/327; 530/360; 530/361; 530/365; 530/366
(58) Field of Search ................ 514/2, 12, 14, 514/18; 435/252.8, 254.1, 255.1; 530/324, 327, 360, 361, 365, 366

(56) References Cited

FOREIGN PATENT DOCUMENTS

WO   WO 90/13642      11/1990
WO   WO-9608269 A1 *  3/1996   .......... A61K/38/17

OTHER PUBLICATIONS

Voet et al., Biochemistry, pp. 112–113 John Wieley & Sons, 1990.*

Wayne Bellamy, "Identification of the Bactercidal Domain of Lactoferrin", pp. 130–136 Biochimica Et Biophysica Acta, NL, Amsterdam (1992).

Wayne Bellamy, "Antibacterial Spectrum of Lactoferricin B, a Potent Bactericidal Peptide Derived from the—Terminal Region of Bovine Lactoferrin", pp. 472–479, Journal of Bacteriology, US, Washington, DC, (1992).

Ametani, E.A.: "Antibody Response of Three Different Strains of Mice to Alpha–S1–Casein Analyzed by Using Proteolytic and Synthetic Peptides", *Biochemical and Biophysical Research Communications*, vol. 154, No. 3 (Aug. 15, 1988), pp. 876–882.

Spuergin, P. et al.: Allergenic Epitopes of Bovine.Alpha.S1–Casein Recognized by Human IgE and IgG, *Allergy* (Copenhagen) (1996), 51 (5), 306–312 Coden: LLRGDY: 0105–4538, 1996.

Database WPI, Section Ch, Week 9439, Derwent Publications Ltd., London, GB; An 94–313708 & JP 06 239 888 A (Kanebo Ltd.) (Aug. 30, 1994), see abstract.

(List continued on next page.)

*Primary Examiner*—Jon Weber
*Assistant Examiner*—Chih-Min Kam
(74) *Attorney, Agent, or Firm*—Jacobson Holman PLLC (57) ABSTRACT

Pepetides having bifidogenic properties are obtainable by the process of adding proteases to cow'milk or human milk, followed by incubation, centrifugation, acidification, purification by reverse phase HPLC and cation-exchange HPLC, culturing *Bifidobacterium bifidum* and *E. coli* in the presence of collected bifidogenic fractions, and isolation of the peptides having bifidogenic properties, and the isolated peptides can be amidated, acetylated, sulfated, phosphorylated, glycosylated, oxidized, or fragmented and still maintain their bifidogenic properties, and combination peptides having bifidogenic properties are obtainable by chemically bonding the peptides having bifidogenic properties, the amidated, acetylated, sulfated, phosphorylated, glycosylated, oxidized, or fragmented peptides having bifidogenic properties, or combinations thereof.

10 Claims, 4 Drawing Sheets

OTHER PUBLICATIONS

Kizawa: "Calmodulin Binding Peptide Comprising Alpha–Casein Exorphin", *J.Agric.Food.Chem.*, vol. 45, No. 5, May 1997, pps. 1579–1581.

Bellamy, E.A.: "Antibacterial Spectrum of Lactoferricin b, A Potent Bactericidal Peptide Derived From the N–Terminal Region of Bovine Lactoferrin", *J. Applied Bacteriology*, vol. 73, No. 6, 1992, pps. 472–479.

Etienne E.A.: "Growth Promotion of Bifidobacterium Animalis by Bovine Milk Proteose–Peptone", *LAIT*, vol. 74, 1994, pps. 313–323.

Proulx, E.A.: "Comparison of Bifidobacterial Growth–Promoting Activity of Ultrafiltered Casein Hydrolyzate Reactions", *LAIT*, vol. 74, 1994, pps. 139–152.

* cited by examiner

Figure 2

Figure 3

SEQUENCE LISTING

<160> NUMBER OF SEQ ID NOS: 24

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 1

Glu Gln Leu Leu Arg Leu Lys Lys
 1               5

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 2

Tyr Leu Glu Gln Leu Leu Arg Leu Lys Lys Tyr
 1               5                  10

<210> SEQ ID NO 3
<211> LENGTH: 8
<212> TYPE: PRT

-continued

```
<213> ORGANISM: Artificial Sequence
<220> FEATURE:
<223> OTHER INFORMATION: Description of Artificial Organism: Synthetic
      bifidogenic peptide

<400> SEQUENCE: 3

Asn Arg Gln Arg Asn Ile Leu Arg
  1               5

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 4

Tyr Met Asn Gly Met Asn Arg Gln Arg Asn Ile Leu Arg
  1               5                  10

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 5

Phe Gln Trp Gln Arg Asn Met Arg Lys
  1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 6

His Thr Gly Leu Arg Arg Thr Ala
  1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 7

Phe Thr Ala Ile Gln Asn Leu Arg Lys
  1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 8

Glu Val Ala Ala Arg Ala Arg Val Val Trp
  1               5                  10
```

```
<210> SEQ ID NO 9
<211> LENGTH: 8
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 9

Trp Gln Arg Asn Met Arg Lys Val
 1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 10

Leu Ala Arg Thr Leu Lys Arg Leu Lys
 1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 11

Tyr Lys Gln Lys Val Glu Lys Val
 1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 12

Leu Val Arg Tyr Thr Lys Lys Val
 1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 13

Lys Tyr Leu Tyr Glu Ile Ala Arg Arg
 1               5

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Organism: Synthetic
      bifidogenic peptide
```

-continued

```
<400> SEQUENCE: 14

Ala Arg Arg Ala Arg Val Val Trp Cys Ala Val Gly
  1               5                  10

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 15

Cys Ile Ala Leu
  1

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 16

Ala Arg Arg Ala Arg Val Val Trp Cys Ala Val Gly Glu
  1               5                  10

<210> SEQ ID NO 17
<211> LENGTH: 55
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 17

Tyr Gln Arg Arg Pro Ala Ile Ala Ile Asn Asn Pro Tyr Val Pro Arg
  1               5                  10                  15

Thr Tyr Tyr Ala Asn Pro Ala Val Val Arg Pro His Ala Gln Ile Pro
                 20                  25                  30

Gln Arg Gln Tyr Leu Pro Asn Ser His Pro Pro Thr Val Val Arg Arg
             35                  40                  45

Pro Asn Leu His Pro Ser Phe
         50                  55

<210> SEQ ID NO 18
<211> LENGTH: 49
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 18

Gly Arg Arg Arg Arg Ser Val Gln Trp Cys Thr Val Ser Gln Pro Glu
  1               5                  10                  15

Ala Thr Lys Cys Phe Gln Trp Gln Arg Asn Met Arg Arg Val Arg Gly
                 20                  25                  30

Pro Pro Val Ser Cys Ile Lys Arg Asp Ser Pro Ile Gln Cys Ile Gln
             35                  40                  45

Ala
```

-continued

```
<210> SEQ ID NO 19
<211> LENGTH: 48
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 19

Gly Arg Arg Arg Ser Val Gln Trp Cys Ala Val Ser Gln Pro Glu Ala
 1               5                  10                  15

Thr Lys Cys Phe Gln Trp Gln Arg Asn Met Arg Lys Val Arg Gly Pro
            20                  25                  30

Pro Val Ser Cys Ile Lys Arg Asp Ser Pro Ile Gln Cys Ile Gln Ala
        35                  40                  45

<210> SEQ ID NO 20
<211> LENGTH: 49
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 20

Gly Arg Arg Arg Arg Ser Val Gln Trp Cys Ala Val Ser Gln Pro Glu
 1               5                  10                  15

Ala Thr Lys Cys Phe Gln Trp Gln Arg Asn Met Arg Lys Val Arg Gly
            20                  25                  30

Pro Pro Val Ser Cys Ile Lys Arg Asp Ser Pro Ile Gln Cys Ile Gln
        35                  40                  45

Ala

<210> SEQ ID NO 21
<211> LENGTH: 26
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 21

Val Tyr Gln His Gln Lys Ala Met Pro Lys Pro Trp Ile Gln Pro Lys
 1               5                  10                  15

Thr Lys Val Ile Pro Tyr Val Arg Tyr Leu
            20                  25

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 22

Ala Arg Arg Ala Arg Val Val Trp Ala Ala Val Gly
 1               5                  10

<210> SEQ ID NO 23
<211> LENGTH: 10
<212> TYPE: PRT
<213> ORGANISM: Artificial Sequence
<220> FEATURE:
```

```
-continued

<223> OTHER INFORMATION: Description of Artificial Organism: Synthetic
      bifidogenic peptide

<400> SEQUENCE: 23

Cys Ala Val Gly Gly Gly Cys Ile Ala Leu
 1               5                  10

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Organism: Synthetic
      bifidogenic peptide

<400> SEQUENCE: 24

Arg His Thr Arg Lys Tyr Trp Cys Arg Gln Gly Ala Arg Gly Gly Cys
 1               5                  10                  15

Ile Thr Leu
```

BIFIDOGENIC PEPTIDES

The present application is a 371 of PCT/EP98/05899, filed Sep. 16, 1998, which claims the priority of German Application No. 19740604.1, filed Sep. 16, 1997, and German Application No. 19805385.1, filed Feb. 11, 1998.

The present invention relates to bifidogenic peptides, a process for their preparation and the use of said bifidogenic peptides.

Milk is known to promote the health of infants. This is often attributed to the influence of milk on the formation of an infant-typical intestinal flora of which more than 90% consists of *Bifidobacterium bifidum*.

It has been the object of the present invention to provide peptides which have a positive influence on the intestinal flora.

This object is achieved by peptides having the features of claim 1. The peptides according to the invention are peptides obtainable by adding proteases to cow's milk or human milk, followed by incubation for two hours;

centrifugation to remove milk fat;

acidification to a pH of 2.0 with strong acids;

removing the precipitated proteins;

application of at least one reverse phase HPLC step;

application of a cation-exchange HPLC step;

collecting fractions;

adjusting the fractions to a salt content of <25 mM by dialysis or reverse phase HPLC for performing activity tests;

culturing *Bifidobacterium bifidum* and *E. coli* in the presence of the fractions and selecting fractions which meet the requirement:

$$\frac{BW}{B0} - \frac{EW}{E0} \geq 0.15 \text{ (bifidogenic)}$$

wherein BW represents the germ count obtained upon 16 hours of incubation of *Bifidobacterium bifidum* in 50% Elliker broth in the presence of the peptides in a concentration of 200 µg/ml;

B0 represents the germ count obtained in the control incubation without active substances;

EW represents the germ count obtained upon 16 hours of incubation of *E. coli* in 3 g/l tryptic soy broth in the presence of the peptides in a concentration of 200 µg/ml;

E0 represents the germ count obtained in the control incubation without active substances;

isolation of the peptide contained in this fraction;

and the amidated, acetylated, sulfated, phosphorylated, glycosylated, oxidized derivatives or fragments thereof having bifidogenic properties.

The peptides according to the invention have an antimicrobial effect against bacteria which do not occur, or only so in small amounts, in the natural infantile intestinal flora, and they promote the growth of desired bacteria, such as *bifidobacteria*, by proriboting the growth of *bifidobacteria* more than that of other bacteria or by selectively inhibiting the undesired bacteria. This property of providing *bifidobacteria* with an advantage with respect to growth is called "bifidogenic".

Preferably, peptides are used which have he following amino acid sequences:

$R_1$-EC1LLRLKK-$R_2$ (SEQ ID NO: 1),
$R_1$-YLEQLLRLKKY-$R_2$ (SEQ ID NO: 2), $R_1$-NHQRNILR-$R_2$ (SEQ ID NO: 3),
$R_1$-YMNGMNRQRNILR-R (SEQ ID NO: 4), $R_1$-FC1WQRNMRK-$R_2$ (SEQ ID NO: 5),
$R_1$-HTGLRRTA-$R_2$ (SEQ ID NO: 6), $R_1$-FTAIQNLRK-$R_2$ (SEQ ID NO: 7),
$R_1$-EVAARARVVW-$R_2$ (SEQ ID NO: 8), $R_1$-WC1RNMRKV-$R_2$ (SEQ ID NO: 9),
$R_1$-LARTLKRLK-$R_2$ (SEQ ID NO: 10), $R_1$-YHQKVEKV-$R_2$ (SEQ ID NO: 11),
$R_1$-LVRYTKKV-$R_2$ (SEQ ID NO: 12), $R_1$-KYLYEIARR-$R_2$ (SEQ ID NO: 13), $R_1$-ARRARVVWCAVG-$R_2$ (SEQ ID NO: 14),
|
$R_3$-CIAL-$R_4$ (SEQ ID NO: 15)

$R_1$-ARRARVVWCAVGE-$R_2$ (SEQ ID NO: 16),
|
$R_3$-CIAL-$R_4$ (SEQ ID NO: 15)

$R_1$-YC1RRPAIAINNPYVPRTYYANPAVVRPHAQIPQRQYLPNSHPPTVVRRPNLHPSF-$R_2$, (SEQ ID NO: 17)

$R_1$-GMRRRSVQWC*TVSQPEATKCFQWQRNMRR*VRGPPVSCIKRDSPIQCIQA-$R_2$, (SEQ ID NO: 18), $R_1$-GMRRSVQWCAVSQPEATKCFQWQRNMRKVRGPPVSCIKRDSPIQCIQA-$R_2$, (SEQ ID NO: 19), $R_1$-GMRRRSVQWCAVSQPEATKCFQWQRNMRKVRGPPVSCIKRDSPIQ CIQA-R, (SEQ ID NO: 20), $R_1$-VYQHQKAMPKPWIQPKTKVIPYVRYL-$R_2$ (SEQ ID NO: 21), $R_1$-AHRARVVWAAVG-$R_2$ (SEQ ID NO: 22),

R₁-CAVGGGCIAL-R₂ (SEQ ID NO: 23), or

R₁-RHTRKYWCRQGARGGCITL-R₂ (SEQ ID NO: 24), wherein
$R_1$, $R_3$ independently represents $NH_2$, an amino acid, or a peptide containing up to 100 amino acids, and
$R_2$, $R_4$ independently represents COOH, $CONH_2$, an amino acid, or a peptide containing up to 100 amino acids;
and the amidated acetylated, sulfated, phosphorylated, glycosylated, oxidixed derivatives or fragments thereof having bifidogenic properties.

Preferably, $R_1$, $R_2$, $R_3$ and $R_4$ have a length of up to 50, more preferably up to 20 and most preferably up to 10 amino acids.

The peptides according to the invention can be obtained by isolation and purification from cow's milk or human milk. Alternatively, they may also be expressed in genetically engineered organisms or prepared by chemical peptide synthesis.

Another aspect of the invention is the nucleic acids coding for the bifidogenic bacteria and antibodies directed against bifidogenic peptides.

The peptides and/or nucleic acids according to the invention can be contained in medicaments together with pharmaceutically acceptable excipients.

In this case, those galenic formulations and dosage forms are selected in which the peptides reach their site of action undegraded.

Preferably, the peptides according to the invention are employed in amounts of from 0.1 to 100 mg per kg of body weight. Effective amounts of nucleic acids are, for example, from 0.01 mg to 100 mg per kg of body weight. Preferably, this amount is within a range of from 1 to 10 mg per kg of body weight for the peptides and nucleic acids.

The peptides according to the invention may also be contained in foods together with nutrients.

In addition, the peptides according to the invention and/or the antibodies directed against the peptides may also be contained in diagnostic agents together with other auxiliary agents.

The peptides and nucleic acids according to the invention are suitable for the treatment of diseases caused by misplaced microbial colonizations, such as infections, inflammations, microbially induced tumors, microbially caused degenerative diseases, diarrheic diseases, colics, deviations in the oral, intestinal and vaginal floras, caries. The misplaced microbial colonization may be caused, for example, by bacteria, fungi, yeasts, protists, viruses, mycoplasmas, filariae and/or plasmodiums.

The peptides according to the invention are also suitable as auxiliary agents in the food preparation in terms of fermentations aids.

In particular, two or more peptides are preferably used in common, or peptides are used which have two or more of the peptide sequences according to the invention. When resistances of microorganisms occur, the different ranges of activity of the individual substances or of the substances having individual sequences of the peptides according to the invention allow to achieve an optimum inhibition of the undesired microorganisms through an appropriate combination of sequences or through a combination of individual substances.

The following Examples are intended to further illustrate the invention:

EXAMPLE 1

Treatment of milk

To human milk, after having been adjusted to pH 3.5 with HCl, was added pepsin (20 mg per g of protein). The enzymatic reaction was incubated at 37° C. for two hours, and stopped by five minutes of boiling. This was followed by centrifugation (20 min, 60,000 g at 4° C.) and skimming off of the milk fat. To the resultant solution was added 0.1% TFA, and centrifugation was again performed to separate off precipitated high molecular weight proteins.

HPLC purification of a bifidogenic peptide from milk

For the purification of bifidogenic peptides from milk, several HPLC separation methods have to be combined in order to achieve preparation in as high a purity as possible through an optimum separation efficiency and to separate off inactive, undesired components. The respective samples formed after each separation step must be tested in two test systems, i.e., a growth test with *bifidobacteria* In combination with a growth test with *E. coli* as a target (see Examples 3 and 4). For the purification, it is necessary to combine at least one reverse phase chromatographic step (preferably two reverse phase chromatographic steps) with a cation-exchange HPLC separation. In the biotests, the respective sample must be employed in a salt-poor condition in order to obtain as optimal a screening result as possible.

Figure 1:
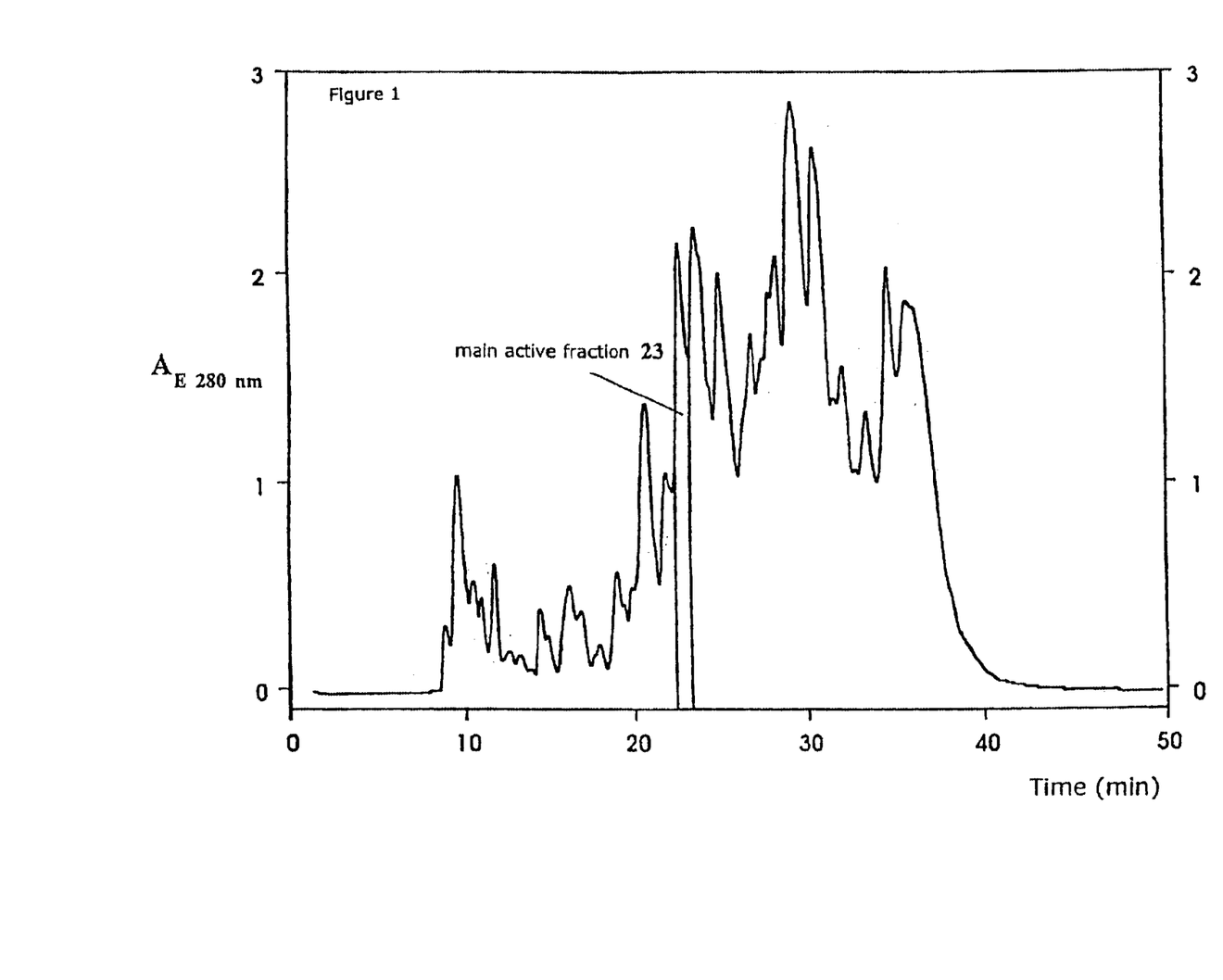
Figure 2:
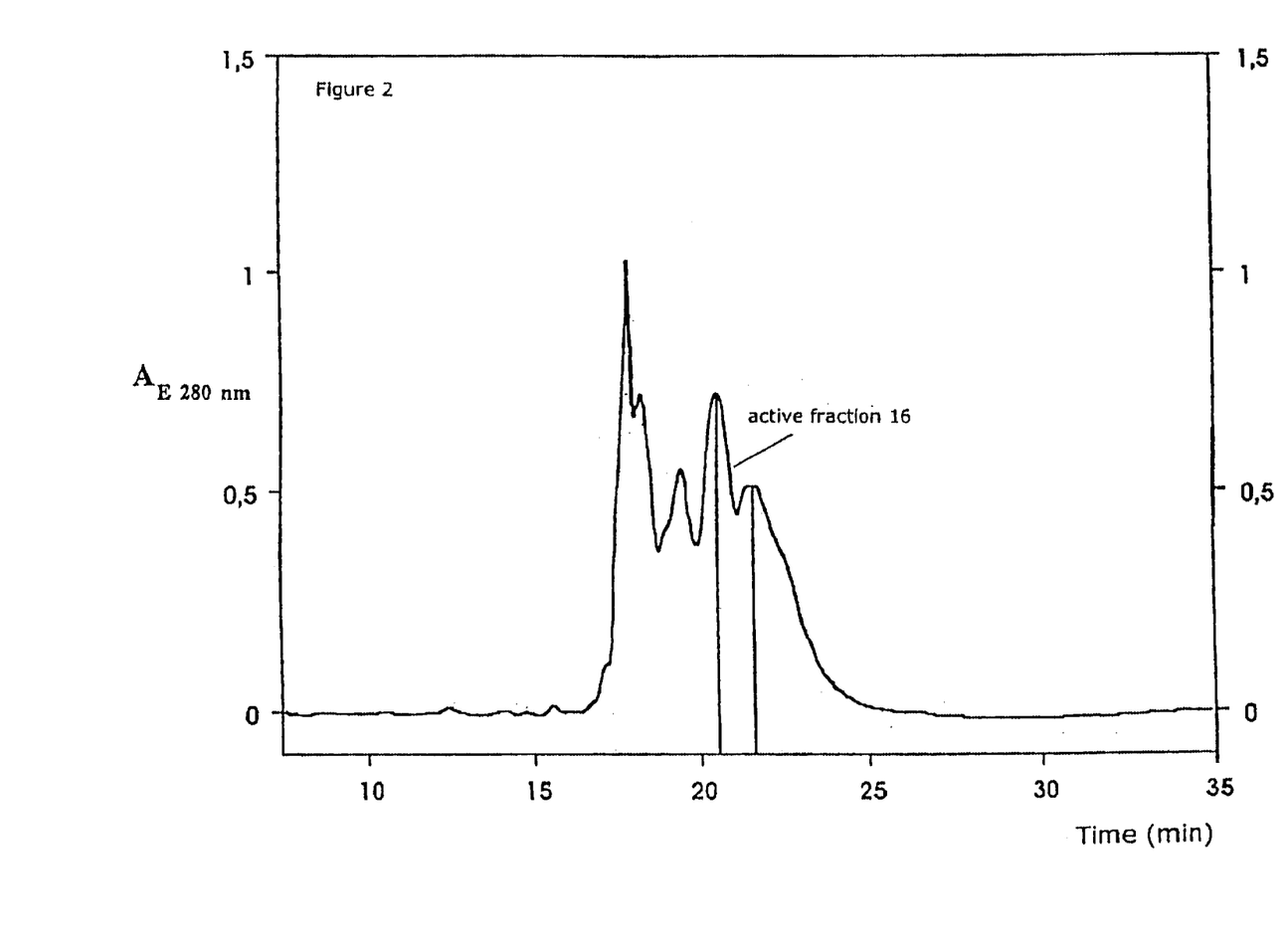
Figure 3:
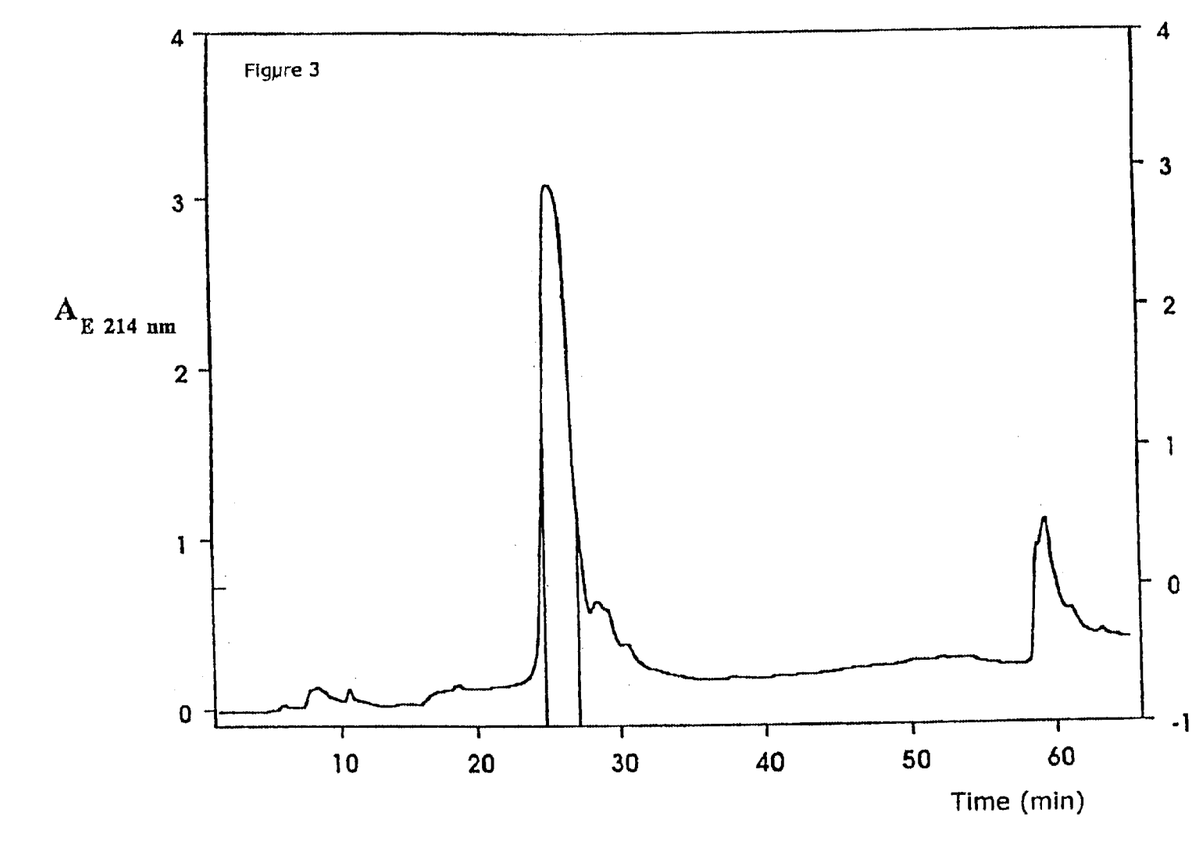
Figure 4:
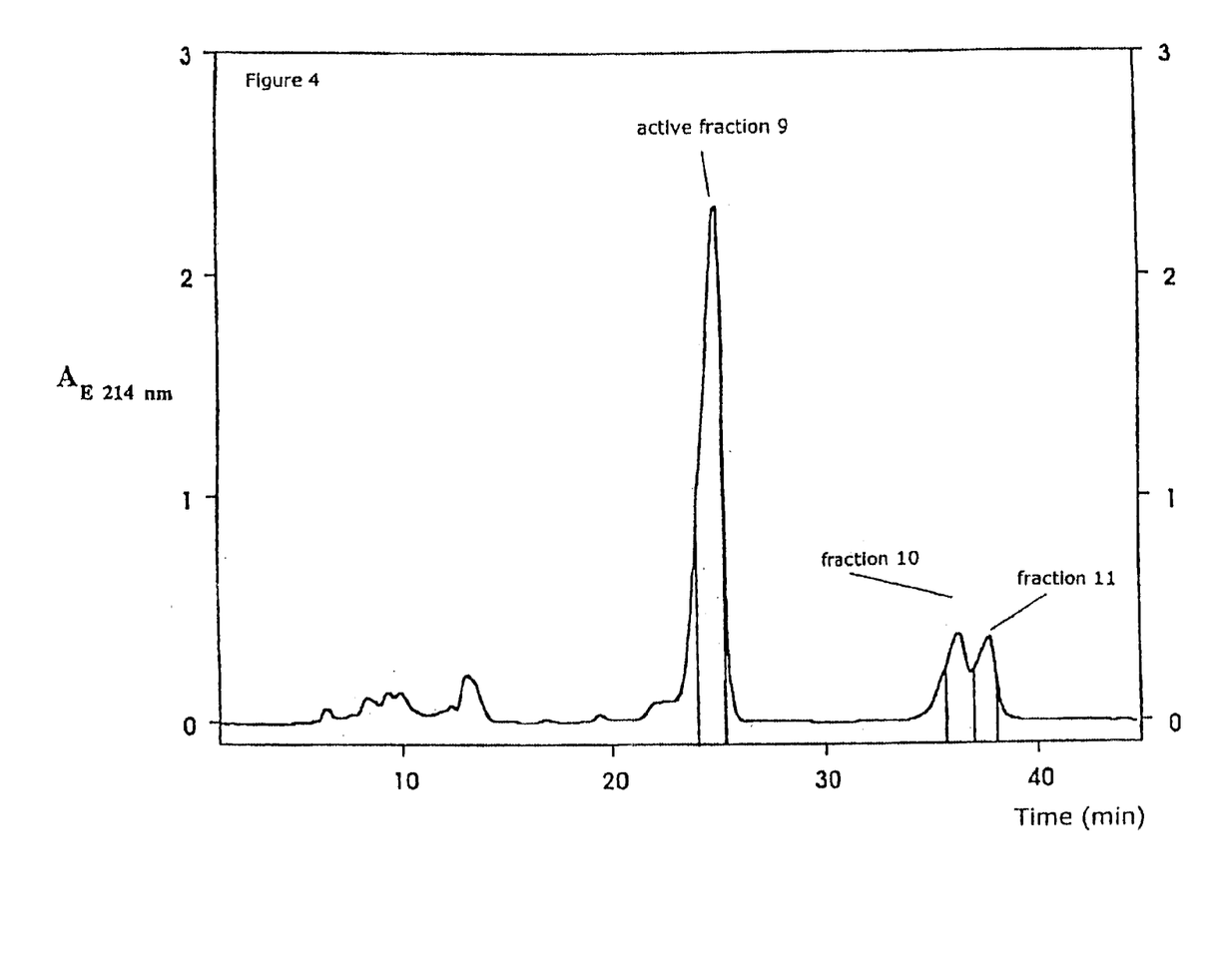

The first separation step was performed by means of a Parcosil C18 column (1×12.5 cm, 100 Å, Biotek, Heidelberg, Germany).
Buffer A: 0.1% TFA
Buffer B: acetonitrile with 0.1% TFA
Gradient: 0 to ⁶0% B in 45 minutes
Flow rate: 2 ml/min
  Detection at 280 nm (see FIG. 1)
  Rechromatography of fraction 23 with the same column and a more gently rising gradient (see picture):
Buffer A: 0.1% TFA
Buffer B: acetonitrile with 0.1% TFA
Gradient: 0 to 20% B in 5 minutes 20 to 50% B in 45 minutes
  Detection at 214 nm (see FIG. 2)
  Rechromatography of fraction 16 from the preceding separation step with the same column, but another eluent, in order to change the selectivity in the separation:
Buffer A: 0.1% TFA
Buffer B: 0.1% TFA in methanol
Gradient: 0 to 40% B in 5 minutes 40 to 70% B in 45 minutes
  Detection at 214 nm (see FIG. 3)
  Rechromatography of the active fraction 21 by cation-exchange HPLC:
Column: Parcosil Pepkat, 4×50 mm, 300 Å, 5 μm, Biotek, Heidelberg
Buffer A: 10 mM phosphate buffer, pH 4.5
Buffer B: buffer A with 1 M NaCl
Flow rate: 0.75 ml/min
Gradient: 0 to 15% B in 5 minutes 15 to 50% B in 35 minutes
Detection at 214 nm (see FIG. 4)
  Each of the fractions obtained was separately desalted in a brief reverse phase HPLC run prior to being passed to the test for antimicrobial and bifidogenic activities.

The following peptides were identified by mass spectrometry and amino acid sequencing:
Fraction 9 contained the pure bifidogenic component (SEQ ID NO: 17):
YQRRPAIAINNPYVPRTYYANPAVVR-PHAQIPQRQYLPNSHPPTVVRRPLPSF (casein K-63-117);
fraction 10 contained the bifidogenic component (SEQ ID NO: 19):
GRRRRSVQWCAVSQPEATKCFQWQRNM-RKVRGPPVSCIKRDSPICCIQA (neutrophile lactoferrin-20-67);
and fraction 11 contains the bifidogenic component with an adduct mass of +16, which indicates that it is an oxidation product (probably, one methionine has been oxidized).
Both peptides and the oxidation product exhibit bifidogenic activity.

EXAMPLE 2

Demonstration of the growth-regulating activity on *E. coli*

Fractions from the HPLC were employed with *E. coli* K12. The test is performed in 3 g/l tryptic soy broth (Sigma) as follows:

For each assay, cultures of *E. coli* K12 were freshly inoculated in tryptic soy broth (Sigma, Deisenhofen, Germany, order No. T8907) (Difco Manual, 10th ed., p. 1027). The incubation of these bacteria was always performed under aerobic conditions at 37° C. for 16 hours. Peptides to be tested were given to a test solution consisting of 200 µl of 3 g/l tryptic soy broth in 96-well cell culture plates, and inoculated with 20 pi of a diluted bacterial suspension. The photometric absorption of the inoculum was 0.05, measured at 500 nm. The growth of the bacteria under the influence of the peptides was also photometrically determined in an ELISA reader after 16 hours and manually determined by microscopy.

EXAMPLE 3

Demonstration of the growth-regulating activity on *Bifidobacterium bifidum*

For each assay, cultures of *Bifidobacterium bifidum* ATCC 29521 were freshly inoculated in Elliker broth (Difco, Detroit, USA) (tryptone 20 g, yeast extract 5 g, gelatin 2.5 g, dextrose 5 g, lactose 5 g, saccharose 5 g, sodium chloride 4 g, sodium acetate 1.5 g, ascorbic acid 0.5 g). The incubation of these bacteria was always performed under anaerobic conditions at 37° C. for 16 to 18 hours. Peptides to be tested were given to a test solution consisting of 200 µl of 50% Elliker broth in 96-well cell culture plates, and inoculated with 20 µl of a diluted bacterial suspension. The photometric absorption of the inoculum was 0.05, measured at 550 nm. The growth of the bacteria under the influence of the peptides was also photometrically determined in an ELISA reader after 16 hours and manually determined by microscopy. N-Acetylglucosamine served as a positive control. Only bifidus cultures which respond to N-acetylglucosamine can be used for this test. After some passages, *bifidobacteria* lose this property; in this case; they can no longer be used for this growth test.

EXAMPLE 4

Those fractions in which the value $$\frac{BW}{B0} - \frac{EW}{E0} \geq 0.15 \text{ (bifidogenic)}$$

were identified as being bifidogenic.

What is claimed is:

1. A pure peptide having bifidogenic properties, and wherein the peptide is an amino acid sequence selected from the group consisting of:

a) EVAARARVVW (SEQ ID NO: 8), b) ARRARVVWAAVG (SEQ ID NO: 22), c) ARRARVVWCAVG (SEQ ID NO: 14), and
   |
   CIAL (SEQ ID NO: 15)

d) ARRARVVWCAVGE (SEQ ID NO: 16)
   |
   CIAL (SEQ ID NO: 15).

2. A peptide according to claim 1 selected from the group consisting of SEQ ID NO: 8 and SEQ ID NO: 22.

3. A medicament containing at least one peptide according to claim 1.

4. A medicament containing least one peptide according to claim 2.

5. A pure peptide having bifidogenic properties and selected from the group consisting of SEQ ID NO: 14 and SEQ ID NO: 16.

6. A medicament containing at least one peptide according to claim 5.

7. A pure peptide having bifidogenic properties, and wherein the peptide is an amino acid sequence selected from the group consisting of:

EVAARARVVW (SEQ ID NO: 8),

ARRARVVWCAVG (SEQ ID NO: 14),
       |
       CIAL (SEQ ID NO: 15)
ARRARVVWCAVGE (SEQ ID NO: 16),
       |
       CIAL (SEQ ID NO: 15)
GRRRSVQWCAVSQPEATKCFQWQRNMRKVRGPPVSCIKRDSPIQCIQA (SEQ ID NO: 19),
       |___________|        |_____________________|

ARRARVVWAAVG (SEQ ID NO: 22), and

YQRRPAIAINNPYVPRTYYANPAVVRPHAQIPQRQYLPNSHPPTVVRRPNLHPSF (SEQ ID NO: 17).

8. A pure peptide having bifidogenic properties, and wherein the peptide is an amino acid sequence selected from the group consisting of:

a) EVAARARVVW (SEQ ID NO: 8), b) ARRARVVWCAVG (SEQ ID NO: 14), c) ARRARVVWAAVG (SEQ ID NO: 22), and d) ARRARVVWCAVG (SEQ ID NO: 14)
   |
   CIAL (SEQ ID NO: 15).

9. A composition for human administration comprising the peptide of claim 7 in combination with a physiologically acceptable excipient in a galenic formulation.

10. A composition for human administration comprising the peptide of claim 8 in combination with a physiologically acceptable excipient in a galenic formulation.

* * * * *

UNITED STATES PATENT AND TRADEMARK OFFICE
CERTIFICATE OF CORRECTION

PATENT NO.    : 6,849,593 B1
DATED         : February 1, 2005
INVENTOR(S)   : Forssmann et al.

It is certified that error appears in the above-identified patent and that said Letters Patent is hereby corrected as shown below:

Title page,
Item [73], Assignee, change "Hanover" to -- Hannover --.

Signed and Sealed this

Tenth Day of May, 2005

JON W. DUDAS
*Director of the United States Patent and Trademark Office*